United States Patent [19]

Buckman et al.

[11] 3,959,328

[45] May 25, 1976

[54] HALOGENATED PROPYL ESTERS OF CYANODITHIOIMIDOCARBONIC ACID

[75] Inventors: Stanley J. Buckman, Memphis; Joseph G. E. Fenyes, Germantown; John D. Pera, Memphis, all of Tenn.

[73] Assignee: Buckman Laboratories, Inc., Memphis, Tenn.

[22] Filed: Apr. 14, 1975

[21] Appl. No.: 568,069

[52] U.S. Cl. .................. 260/453 RW; 424/298; 106/15 R; 8/115.6; 252/8.1; 428/411
[51] Int. Cl.² .................................... C07C 119/06
[58] Field of Search .............. 71/100; 260/453 RW; 424/298; 117/137; 106/15; 8/115.6; 252/8.1

[56] References Cited
UNITED STATES PATENTS

| | | | |
|---|---|---|---|
| 2,430,332 | 11/1947 | Guy | 71/100 |
| 3,299,129 | 1/1967 | D'Amico | 260/453 RW |
| 3,658,901 | 4/1972 | Timmons et al. | 260/453 RW |
| 3,692,882 | 9/1972 | Gutman | 260/453 RW |

OTHER PUBLICATIONS

Timmons et al., J. Org. Chem. Vol. 32, pp. 1566–1572, (1966).

*Primary Examiner*—Lewis Gotts
*Assistant Examiner*—D. R. Phillips
*Attorney, Agent, or Firm*—Floyd Trimble

[57] ABSTRACT

Halogenated propyl esters of cyanodithioimidocarbonic acid are useful for inhibiting the growth and proliferation of bacteria, fungi and nematodes.

6 Claims, No Drawings

HALOGENATED PROPYL ESTERS OF CYANODITHIOIMIDOCARBONIC ACID

This invention relates to novel compositions of matter and the use of the same as bactericides, fungicides, algicides, nematocides, and preservatives in industry and agriculture. More particularly, the present invention relates to compounds identified as bromo- and chloropropyl esters of cyanodithioimidocarbonic acid.

The compositions of this invention are characterized by the formula:

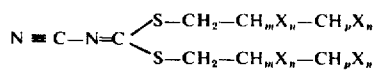

$$N \equiv C-N=C \begin{matrix} S-CH_2-CH_mX_n-CH_pX_n \\ S-CH_2-CH_mX_n-CH_pX_n \end{matrix}$$

wherein $n$ is the same and equal to 1 or 2, $m$ is 0 or 1, $p$ is 1 or 2, and X is bromine or chlorine. The specific compounds covered by this invention are bis(2,2,3,3-tetrabromopropyl)cyanodithioimidocarbonate, bis(2,2,3,3-tetrachloropropyl)cyanodithioimidocarbonate, bis(2,3-dibromo-2,3-dichloropropyl)cyanodithioimidocarbonate, bis(2,3-dibromopropyl)cyanodithioimidocarbonate, and bis(2,3-dichloropropyl)cyanodithioimidocarbonate.

The compounds of this invention are useful in the treatment of seeds and living plants to control bacterial and fungal diseases, as nematocides, as bactericides and fungicides in the treatment of wood products and wood chips used in pulp manufacture, for slime control in pulp and paper mills, as microbicides and algicides for the treatment of fresh water used in industrial processes, and as microbicides and algicides in cooling towers. In addition, the products are stable in both acid and alkaline systems and are, therefore, useful as preservatives for adhesives; caulking, grouting, spackling compounds, and joint cements; detergents; floor wax emulsions and floor polishes; inks; latex emulsions; laundry starch; cutting fluid emulsions; latex paints; coatings, finishes and printing colors based on starch and latex for pulp and paper; spinning emulsions; finishing solutions and printing pastes used in the textile industry.

When the compounds of this invention are used to treat seeds before planting, suitable quantities vary from 50 to 5000 parts per million parts based on the weight of the seed. When applied to soil to protect seeds already planted and when used as nematocides, suitable quantities vary from about 0.1 to 20 pounds per acre. When applied to foliage of living plants, suitable preparations containing 0.1 to 1.0 percent of the compounds of this invention are uniquely ree of phytotoxicity to the crop plants.

When these compounds are used to treat wood products or wood chips used to manufacture pulp, suitable quantities vary from 1 to 10 pints of a composition containing 30 percent of the compounds of this invention as an active ingredient to 100 gallons of water.

For those uses involving the addition of the bromo- and chloropropyl esters of this invention to aqueous systems, a suitable quantity varies from about 0.01 to 1,000 parts per million parts of water. When used as preservatives, the quantities used will vary from 10 to 10,000 parts per million parts of the product being preserved.

The compounds of this invention are prepared by reacting aqueous or nonaqueous solutions of the alkali metal or alkaline earth metal cyanodithioimidocarbonates will allyl or propargyl chloride or allyl or propargyl bromide at temperatures ranging from 0° to 70° C. The diallyl and dipropargyl cyanodithioimidocarbonates are produced in good yield and are easily separated from the reaction mixtures. These unsaturated compounds are then reacted with bromine or chlorine using conventional procedures to produce the brominated and chlorinated propyl esters of cyanodithioimidocarbonate. The products are viscous oils or solids.

The organic compounds of this invention may be used diluted with a carrier which may be liquid or solid. Dusts may be prepared with a finely divided solid such as talc, clay, pyrophyllite, diatomaceous earth, hydrated silica, calcium silicate, or magnesium carbonate. If desired, wetting and/or dispersing agents may be used. When the proportions of these are increased, there results a wettable powder, which may be dispersed in water and applied from a spray.

Dusts may contain 1 percent to 15 percent of one or more compounds of this invention, while wettable powders may contain up to 50 percent or more of one or more of these compounds.

A typical formulation of a wettable powder comprises 20 percent to 50 percent of the organic compounds, 45 percent to 75 percent of one or more finely divided solids, 1 percent to 5 percent of a wetting agent, and 1 to 5 percent of a dispersing agent. Typical wetting agents include sodium dodecyl sulfate, sodium nonylbenzene sulfonate, sodium dioctyl sulfosuccinate, octylphenoxypolyethoxyethanol, or other nonionic agents, such as ethylene and/or propylene oxide condensates with long chained alcohols, mercaptans, amines, or carboxylic acids. Typical dispersing agents include the sodium sulfonate of condensed naphthaleneformaldehyde and lignin sulfonates.

Liquid concentrates may also be used. These are prepared by taking up the organic compounds in an organic solvent together with one or more surface active agents. For example, there may be mixed 60 parts of one of the organic compounds, 20 parts of a surface-active solvent-soluble alkylphenoxypolyethoxyethanol and 20 parts of aromatic mineral spirits or xylene.

The compounds of this invention may be used in conjunction with other fungicidal agents and also in conjunction with miticides or insecticides or other pesticides.

The compounds of this invention also have exhibited fire-retardant properties when tested in paints, paper, plastics and textiles.

In order to disclose the nature of the invention still more clearly, the following illustrative examples will be given. It is understood, however, that the invention is not to be limited to the specific conditions or details set forth in these examples, except insofar as such limitations are specified in the appended claims.

EXAMPLE 1

Preparation of diallyl cyanodithioimidocarbonate

A 250-milliliter reaction flask was charged with 98.8 grams of 32.8 percent aqueous solution of disodium cyanodithiomidocarbonate (0.2 mole) and 30.6 grams (0.4 mole) of allyl chloride was slowly added with vigorous stirring. The exothermic reaction proceeded smoothly, the temperature rising to 55° C. After all the allyl chloride was introduced, stirring was continued at 40°–45° C. for an additional 1.5 – 2 hours, cooled to room temperature, filtered and the filtrate was transferred into a separatory funnel. After separating the organic layer, the aqueous phase was extracted with ether. The ether extracts were combined with the organic layer, dried over anhydrous magnesium sulfate, filtered and concentrated under reduced pressure to yield 36.1 grams (91.16 percent of the theory) of an orange oil. The produce was identified by characteristic peaks in the infrared spectrum as diallyl cyanodithioimidocarbonate.

EXAMPLE 2

Bis(2,3-dibromopropyl)cyanodithioimidocarbonate

A 19.8 grams (0.1 mole) portion of diallyl cyanodithioimidocarbonate in 60 milliliters of dry chloroform was charged to a vessel. To this solution was added dropwise 32.0 grams (0.2 mole) of bromine. The moderately exothermic reaction proceeded smoothly. After all the bromine was introduced, stirring was continued at ambient temperature for a few hours. After filtration, the chloroform was evaporated at subatmospheric pressure to yield 30.3 grams (58.6 percent of the theory) of an orange oil. The product was identified by characteristic peaks in the infrared spectrum as bis(2,3-dibromopropyl)cyanodithioimidocarbonate.

EXAMPLE 3

Bis(2,3-dichloropropyl)cyanodithioimidocarbonate

A solution of 39.6 grams (0.2 mole) of diallyl cyanodithioimidocarbonate in 150 milliliters of chloroform was placed into a flask and 14.2 grams of chlorine gas was passed under the surface of the stirred solution. The exothermic reaction proceeded smoothly. The mixture was stirred at ambient temperature for 1.5 hours. After filtration, the chloroform was evaporated at subatmospheric pressure to yield 46.3 grams (68.1 percent of the theory) of a dark brown oil. The product was identified by characteristic peaks in the infrared spectrum as bis(2,3-dichloropropyl)cyanodithioimidocarbonate.

EXAMPLE 4

Dipropargyl cyanodithioimidocarbonate was made using the method described in Example 1. Bis(2,2,3,3-tetrabromopropyl)cyanodithioimidocarbonate and bis(2,2,3,3-tetrachloropropyl)cyanodithioimidocarbonate were prepared by treatment of dipropargyl cyanodithioimidocarbonate with bromine and chlorine, respectively, using the general method described in Examples 2 and 3, respectively.

EXAMPLE 5

The two compounds of Examples 2 and 3, bis(2,3-dibromopropyl)cyanodithioimidocarbonate (A) and bis(2,3-dichloropropyl)cyanodithioimidocarbonate (B) were tested against Enterobacter aerogenes using the pulp-substrate procedure described in U.S. Pat. No. 2,881,070 at pH of 5.5, 6.5 and 7.5. The results are tabulated in Table 1.

TABLE 1

Percent kill of Enterobacter aerogenes in a pulp substate at pH 5.5, 6.5 and 7.5 after 18 hours contact

| Concentration based on active ingredients | pH | A | B |
|---|---|---|---|
| Parts per million | | Percent kill | |
| 0.5 | 5.5 | 15 | 26 |

TABLE 1-continued

Percent kill of Enterobacter aerogenes in a pulp substate at pH 5.5, 6.5 and 7.5 after 18 hours contact

| Concentration based on active ingredients | pH | A | B |
|---|---|---|---|
| 1.0 | | 26 | 26 |
| 2.0 | | 99.7 | 0 |
| 3.0 | | 99.9 | 15 |
| 5.0 | | 99.9 | 0 |
| 10.0 | | 99.9 | 40 |
| 15.0 | | 99.9 | 80 |
| 20.0 | | 99.0 | 98 |
| 0.5 | 6.5 | 3 | 0 |
| 1.0 | | 17 | 0 |
| 2.0 | | 98 | 22 |
| 3.0 | | 98 | 13 |
| 5.0 | | 99.9 | 0 |
| 10.0 | | 99.8 | 18 |
| 15.0 | | 99.9 | 73 |
| 20.0 | | 99.9 | 98 |
| 0.5 | 7.5 | 7 | 19 |
| 1.0 | | 0 | 0 |
| 2.0 | | 12 | 16 |
| 3.0 | | 36 | 12 |
| 5.0 | | 85 | 28 |
| 10.0 | | 99.6 | 17 |
| 15.0 | | 99 | 35 |
| 20.0 | | 99.9 | 54 |

EXAMPLE 6

The two compounds of Examples 2 and 3, bis(2,3-dibromopropyl)cyanodithioimidocarbonate (A) and bis(2,3-dichloropropyl)cyanodithioimidocarbonate (B) were tested against the fungi Aspergillus niger, Penicillium roqueforti, and Chaetomium globosum using the pulp substrate method described in U.S. Pat. No. 3,356,706. The period of observation was 14 days. Growth was recorded after this period on the basis of the following key:

4 = excellent growth
3 = good growth
2 = poor growth
1 = very poor growth, scant, questionable
0 = no growth The results are summarized in Table 2.

TABLE 2

Inhibition of Aspergillus niger, Penicillium roqueforti and Chaetomium globosum in a pulp substrate method after 14 days incubation.

| Fungus | Concentraion based on active ingredient | Growth | |
|---|---|---|---|
| | Parts per million | A | B |
| Aspergillus niger | 0 | 4 | 4 |
| | 5 | 4 | 4 |
| | 10 | 4 | 4 |
| | 15 | 3 | 4 |
| | 20 | 0 | 4 |
| | 25 | 0 | 4 |
| | 50 | 0 | 4 |
| | 100 | 0 | 0 |
| Penicillium roqueforti | 0 | 4 | 4 |
| | 5 | 4 | 4 |
| | 10 | 4 | 4 |
| | 15 | 4 | 4 |
| | 20 | 0 | 4 |
| | 25 | 0 | 4 |
| | 50 | 0 | 0 |
| Chaetomium globosum | 0 | 4 | 4 |
| | 5 | 4 | 4 |
| | 10 | 4 | 4 |
| | 15 | 1 | 4 |

TABLE 2-continued

Inhibition of Aspergillus niger, Penicillium roqueforti and Chaetomium globosum in a pulp substrate method after 14 days incubation.

| Fungus | Concentraion based on active ingredient | Growth |  |
|---|---|---|---|
|  | 20 | 1 | 1 |

EXAMPLE 7

The two compounds of Example 2 and 3, bis(2,3-dibromopropyl)cyanodithioimidocarbonate (A) and bis(2,3-dichloropropyl)cyanodithioimidocarbonate (B) were tested against the algae *Chlorella pyrenoidosa*, *Chlorococcum hynosporum* and *Phormidium inundatum* using the method described in Example 2 of U.S. Pat. No. 3,771,989. The period of observation was 14 days. Growth was recorded after this period on the basis of the following key:

4 = excellent growth
3 = good growth
2 = poor growth
1 = very poor growth, scant, questionable
0 = no growth The results are summarized in Table 3.

TABLE 3

Inhibition of the algae Chlorella pyrenoidosa, Chlorococcum hypnosporum and Phormidium inundatum after 14 days.

| Alga | Concentration based on active ingredients | Growth | |
|---|---|---|---|
|  |  | A | B |
| Chlorella pyrenoidosa | 0 | 4 | 4 |
|  | 0.5 | 4 | 4 |
|  | 1.0 | 4 | 4 |
|  | 2.0 | 4 | 4 |
|  | 3.0 | 4 | 4 |
|  | 5.0 | 1 | 4 |
|  | 10.0 | 0 | 2 |
|  | 15.0 | 0 | 1 |
|  | 20.0 | 0 | 0 |
| Chlorococcum hypnosporum | 0.0 | 4 | 4 |
|  | 0.5 | 2 | 4 |
|  | 1.0 | 0 | 2 |
|  | 2.0 | 0 | 0 |
|  | 3.0 | 0 | 0 |
|  | 5.0 | 0 | 0 |
|  | 10.0 | 0 | 0 |
|  | 15.0 | 0 | 0 |
|  | 20.0 | 0 | 0 |
| Phormidium inundatum | 0.0 | 4 | 4 |
|  | 0.5 | 4 | 4 |
|  | 1.0 | 4 | 4 |
|  | 2.0 | 4 | 4 |
|  | 3.0 | 3 | 4 |
|  | 5.0 | 1 | 4 |
|  | 10.0 | 0 | 0 |
|  | 15.0 | 0 | 0 |
|  | 20.0 | 0 | 0 |

While particular embodiments of the invention have been described, it will be understood, of course, that the invention is not limited thereto since many modifications may be made thereof. It is, therefore, contemplated to cover by the appended claims any such modifications as fall within the true spirit and scope of the invention.

The invention having thus been described, what is claimed and desired to be secured by Letters Patent is:

1. A composition of matter having the formula:

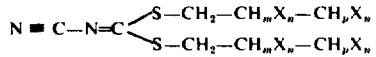

wherein $n$ is the same and equal to 1 or 2, $m$ is 0 or 1, $p$ is 1 or 2, and X is bromine or chlorine.

2. The compound according to claim 1 identified as bis(2,3-dibromopropyl)cyanodithioimidocarbonate.

3. The compound according to claim 1 identified as bis(2,3-dichloropropyl)cyanodithioimidocarbonate.

4. The compound according to claim 1 identified as bis(2,2,3,3,-tetrabromopropyl)cyanodithioimidocarbonate.

5. The compound according to claim 1 identified as bis(2,2,3,3-tetrachloropropyl)cyanodithioimidocarbonate.

6. The compound according to claim 1 identified as bis(2,3-dibromo-2,3-dichloropropyl)cyanodithioimidocarbonate.

* * * * *